United States Patent [19]
Renslow

[11] Patent Number: 6,006,777
[45] Date of Patent: Dec. 28, 1999

[54] MEDIA DISPENSING APPARATUS

[75] Inventor: Bruce E. Renslow, Castaic, Calif.

[73] Assignee: Hanson Research Corporation, Chatsworth, Calif.

[21] Appl. No.: 09/145,318

[22] Filed: Aug. 31, 1998

Related U.S. Application Data

[60] Provisional application No. 60/062,741, Oct. 23, 1997.

[51] Int. Cl.[6] ........................................ B67D 5/00
[52] U.S. Cl. .......................... 137/205; 137/263; 137/544; 137/899
[58] Field of Search .................................. 137/205, 263, 137/597, 899, 544

[56] References Cited

U.S. PATENT DOCUMENTS

| | | | |
|---|---|---|---|
| 494,061 | 3/1893 | DFay . | |
| 666,051 | 1/1901 | Grun | 137/899 |
| 1,563,905 | 12/1925 | Kerckhoff et al. | 137/263 |
| 3,101,771 | 8/1963 | McCuen | 137/263 |
| 5,639,974 | 6/1997 | Hanson et al. | 73/866 |
| 5,832,948 | 11/1998 | Schell | 137/263 |

Primary Examiner—Stephen M. Hepperle
Attorney, Agent, or Firm—Jack C. Munro

[57] ABSTRACT

A mobile media dispensing apparatus in the form of a portable cart which has a plurality of vessels. The apparatus of this invention is to simultaneously deliver to testing vessels of a separate dissolution test apparatus an identical volume of a preheated, filtered, deaerated media within three minutes of time. The media of each vessel is to be used by depositing a pill therein with the dissolution rate to be determined of the pill within the media of each vessel.

7 Claims, 7 Drawing Sheets

MEDIA DISPENSING APPARATUS

REFERENCE TO PRIOR APPLICATION

This application is based on Provisional Patent Application Ser. No. 060/062,741 filed Oct. 23, 1997 by the same title and the same inventor.

BACKGROUND OF THE INVENTION

1. Field of the Invention

The field of this invention relates to dissolution testing equipment for determining the dissolving rate of drugs encapsulated in the form of a tablet, capsule or caplet which are commonly known as pills and more particularly to a media dispensing apparatus to be used in conjunction with a dissolution test apparatus.

2. Description of the Prior Art

Drugs are commonly manufactured in the form of pills. The reason for using pills is that when the drug is swallowed by a human, the drug will be disseminated into the body over a period of time as the pill dissolves. Manufacturers of pills are required by law to determine the precise dissolving characteristics of their pill before it is placed on the market. In order to determine the dissolving characteristics, dissolution test equipment is utilized. Although dissolution test equipment is commonly used in conjunction with drugs designed for human consumption, it is considered to be within the scope of this invention to use it with other animals such as horses, cows, rabbits, cats, dogs, monkeys and so forth.

Every known form of dissolution testing equipment generally utilizes a plurality of liquid containing flasks called testing vessels. In each flask is to be placed a liquid called, media, with the media essentially duplicating the liquid solution that is contained within the stomach of the human body. A precise quantity of the solution is placed within the flask. The pill is then inserted within the flask and the time of the insertion then noted. A mixing paddle is inserted within the flask with mixing at a precise rate then occurring. The mixing procedure is to duplicate the natural turbulence that is created within the stomach of the human. Aliquots are removed from the solution at precise time intervals with these aliquots then being analyzed to determine the amount of drug that has been dissolved within the solution in relation to the time that the pill has been in solution.

In order to insure that the testing process is accomplished as accurately and as quickly as possible, such dissolution testing apparatus in the past has been designed as follows:

1. Normally the dissolution testing apparatus will have six or eight flasks. Dissolution testing of the pill is accomplished simultaneously in all six or eight flasks with each flask to receive a pill. The average dissolving rate is then calculated between the flasks.

2. The flasks are placed in a bath with this bath to be maintained at a precise temperature. The temperature level is to essentially duplicate the temperature of the stomach liquid within the human.

In the past, the procedure in conjunction with the six or eight flasks is for the technician to take media at the precise temperature and fill each flask accurately to a precise level. This precise filling of each of the flasks is difficult if this procedure is completed manually. Additionally, it is important that the media be deaerated, and with this manual filling technique, no deaeration of the media takes place.

In the past, there has been designed a media dispensing apparatus which facilitated the dispensing of a precise quantity of media into each of the flasks of the dissolution test equipment. However, one of the disadvantages of such a piece of equipment in the past has been that it has been not readily portable, therefore could not be easily transported from one dissolution test apparatus to another. Also, the measuring system for determining volume that is being supplied into each flask is not that precise. It is important that each of the flasks within the dissolution test apparatus have exactly the same volume. Also, there was no provision for heating of the media to a precise temperature.

A typical dissolution test apparatus is shown and described within U.S. Pat. No. 5,639,974 which was issued on Jun. 17, 1997. However, the media dispensing apparatus of this patent application can be effectively used with numerous other types of dissolution test apparatus and it is not intended to be used solely with the dissolution test apparatus of the aforementioned patent.

SUMMARY OF THE INVENTION

A portable media dispensing apparatus in the form of a mobile cart which includes a media supply tank and a plurality of vessels to which the media is to be supplied. The media tank includes a heater which heats the media to a precise temperature level. The media is supplied through fill lines simultaneously to each of the vessels so that the exact quantity of media is supplied to each vessel. Each of the vessels is closed to the ambient and a vacuum is drawn in conjunction with each vessel in order to deaerate the media contained within the vessel. The media is then to be pumped from each vessel into similar vessels of a dissolution test apparatus with the quantity of media in each vessel transferred exactly to a similar vessel of the dissolution test apparatus. A valve assembly is mounted in conjunction with each of the fill lines that supply the media to each of the vessels with the same valve assembly operating in conjunction with each of the dispense lines through which is dispensed the media from each of the vessels. The valve assembly is positionable so as to either have fill lines open and the dispense lines closed or with the fill lines closed and the dispense lines open. An overflow vessel is mounted in conjunction with each of the vessels to cause any overflow media being supplied to a vessel to be discharged into the overflow vessel. A filter is mounted in conjunction with the media tank with the media to pass through the filter and be filtered prior to flowing into each of the fill lines.

One of the primary objectives of the media dispensing apparatus of the present invention is to provide a media dispensing apparatus that can be used in conjunction with different manufacturers of dissolution test equipment that provides for quick and easy dispensing of a precise volume of media into each of the testing vessels of a dissolution test apparatus.

Another objective of the media dispensing apparatus of the present invention is to construct a media dispensing apparatus that dispenses a precise quantity of media into each testing vessel within an exceedingly short period of time.

Another objective of the media dispensing apparatus of the present invention is to heat the media that is dispensed to a precise desired temperature prior to being dispensed.

Another objective of the media dispensing apparatus of the present invention is to filter the media prior to being dispensed so as to remove any impurity of significance from the media.

DETAILED DESCRIPTION OF THE PREFERRED EMBODIMENT

Every dissolution lab performs repetitive tests on each drug. The normal procedure once a new pill is constructed is a supply a quantity of the pills to a dissolution testing lab. The dissolution testing lab is to take the pills and deposit each one within a precise quantity of a solution called a media. This media is contained within vessels with a pill to be deposited within each vessel. Aliquots are then sequentially removed from each vessel over preset periods of time to determine the dissolution rate of the drug within that media. This is not just performed once within one vessel but is literally performed hundreds and maybe thousands of times. The dissolution testing apparatus of the aforementioned U.S. Pat. No. 5,639,974 contains eight identical vessels each of which contains a precise quantity of media at a precise temperature. A pill is to be dropped into each vessel and aliquots are then removed from each vessel over a preset period of time to determine the dissolution rate. Before each test can be started in conjunction with the dissolution testing apparatus, a precise quantity of media at a precise temperature is to be deposited within each vessel with the volume in each vessel being essentially identical. The media dispensing apparatus of the present invention is intended for that purpose.

The media dispensing apparatus of the present invention is intended to simultaneously deliver to each vessel of the dissolution testing apparatus a precise quantity, each identical in volume between the vessels, of a preheated, filtered, deaerated media within a very short period of time with this time actually being about three minutes. The tank capacity of the dispensing apparatus is between ten and forty liters. The temperature range of the media is thirty to forty-five degrees centigrade plus or minus 0.5 degrees centigrade. Delivery volume is adjustable to between 250 to 1,000 milliliters in fifty milliliter increments at plus or minus one percent accuracy. Media deaeration is below ninety-five percent saturation when it is delivered to the flask of the dissolution test apparatus.

Figure 1:
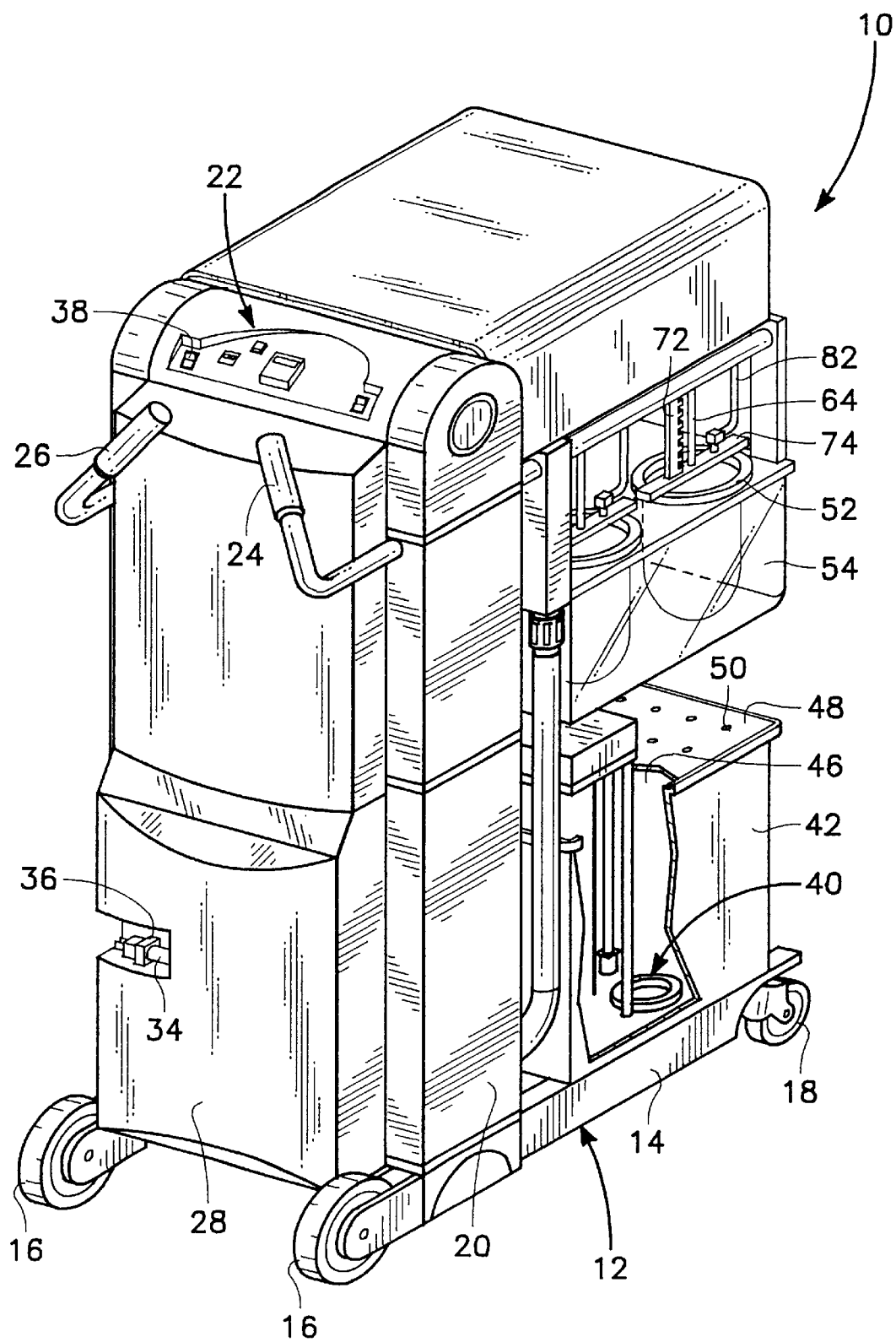
FIG. 1 is a right side positioned rear perspective view of the media dispensing apparatus of the present invention.
Figure 2:
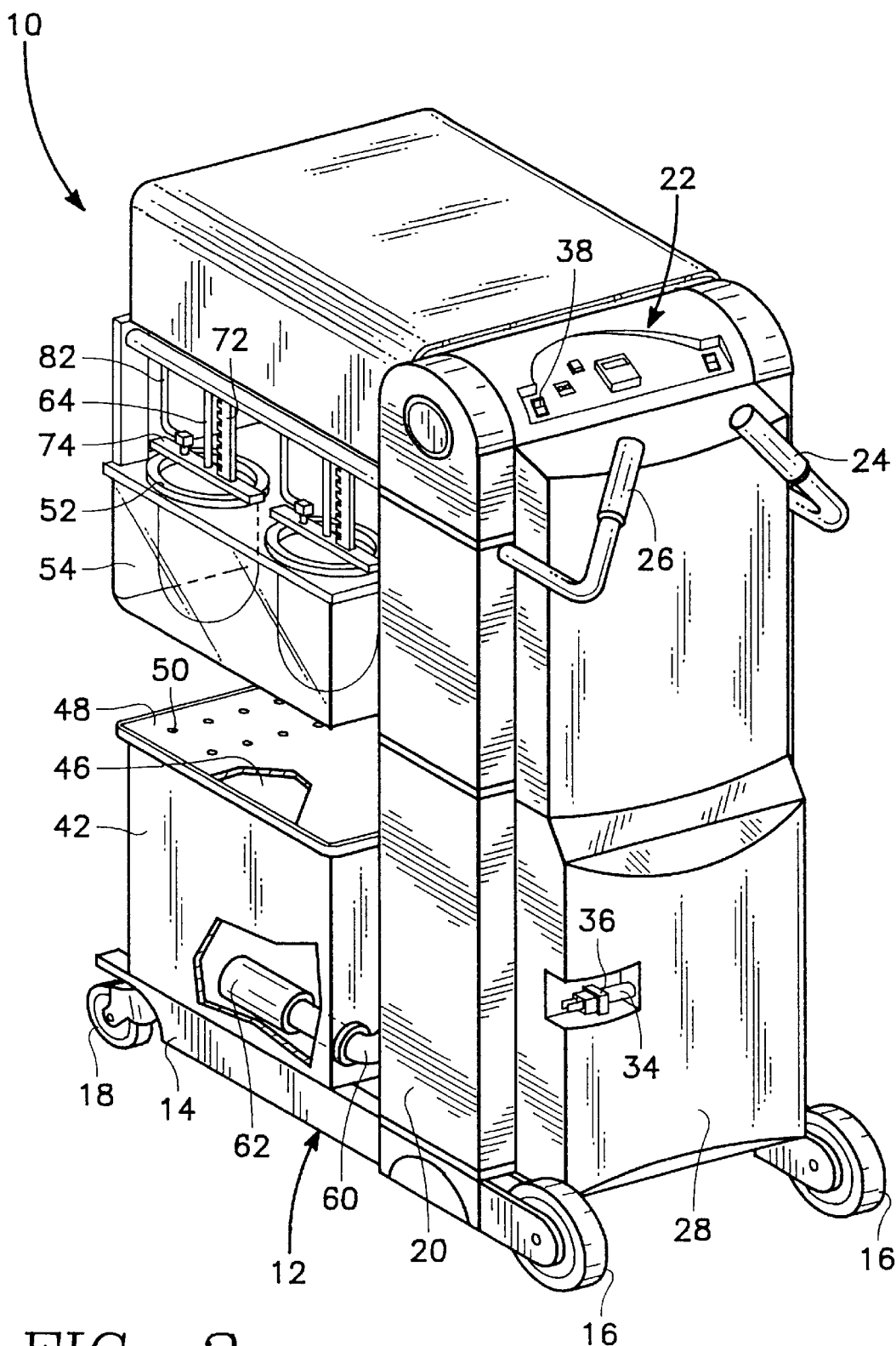
FIG. 2 is a left side positioned front perspective view of the media dispensing apparatus of the present invention.
Figure 3:
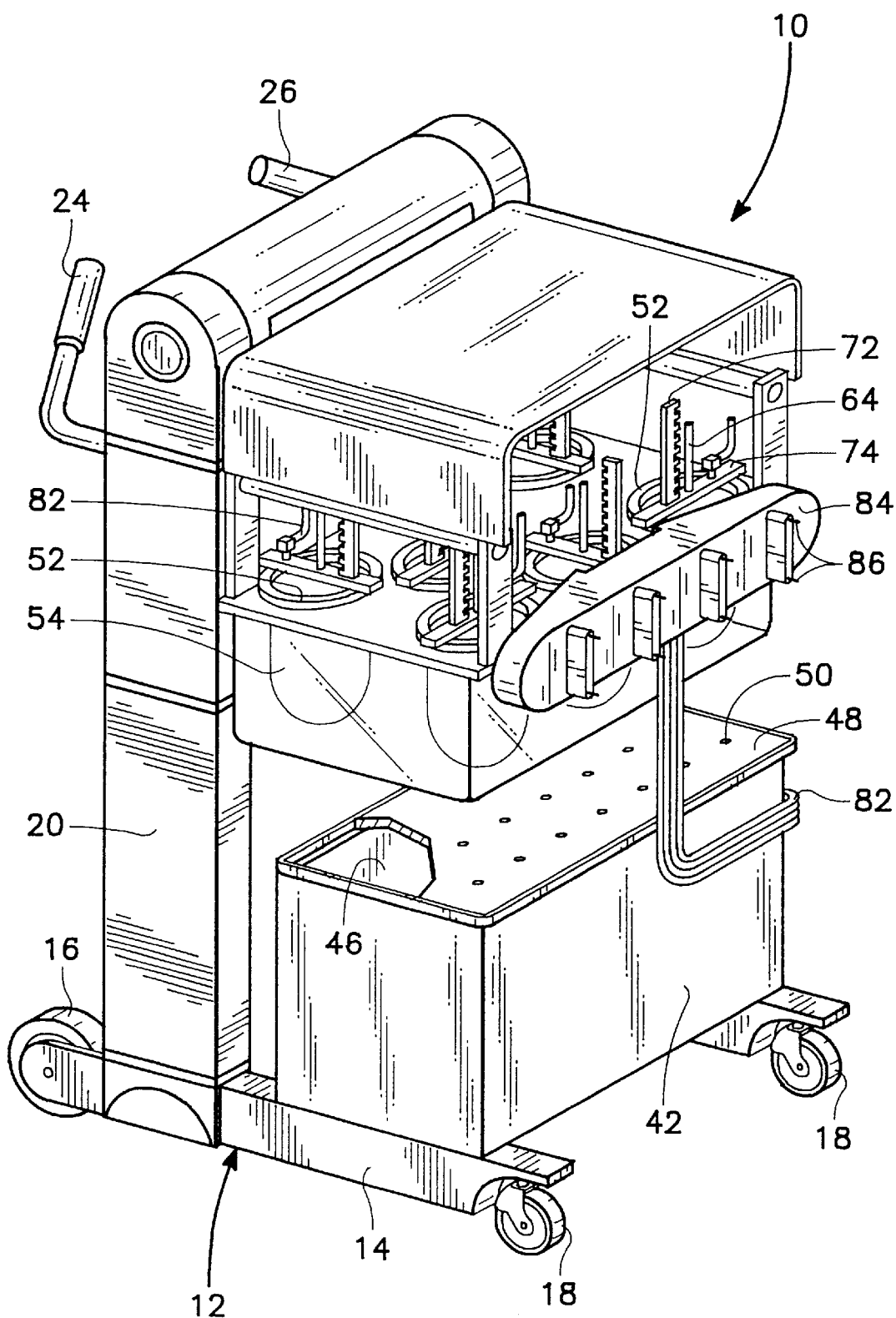
FIG. 3 is a front perspective view of the media dispensing apparatus of the present invention.

Referring particularly to the drawings, there is shown in FIGS. 1–3 the media dispensing apparatus 10 of this invention. The media dispensing apparatus 10 is mounted on a housing in the form of a mobile cart 12. The mobile cart 12 has a base 14 on which are mounted a pair of rear wheels 16 and a pair of front wheels 18. Mounted on the base 14 is an upstanding housing section 20 which terminates in its upper end into a control panel 22. Mounted on the upstanding housing section 20 are a pair of handles 24 and 26. The handles 24 and 26 are for the purpose of manually moving the media dispensing apparatus 10. The media dispensing apparatus 10 is then to be rolled to any desired location. Contained within a cover 28, which is mounted on the base 14, is a pair of pumps 30 and 32. The pumps 30 and 32 are basically identical and have each been selected, although it is not mandatory, to deliver 1.2 cubic feet of air per minute. Pump 30 delivers air at 35 psi and pump 32 delivers air at 10 psi. The vacuum side of pump 30 is continuously open to the atmosphere. It is to be understood that the size of the pumps 30 and 32 could be increased or decreased as desired. Also contained within the cover 28 is an electric cord 34 which is mounted on a retractable cord reel, which is not shown. The electric cord 34 terminates at its outer end in an electric plug 36 which is to be plugged into a source of electricity, which is not shown. The electricity is used to operate the pumps 30 and 32. Mounted on the control panel 22 is a main power switch 38 which is to be initially activated to turn the media dispensing apparatus 10 of this invention to the "on" position. The same main power switch 38 is to be activated to the "off" position when it is desired to deactivate the media dispensing apparatus 10 of this invention.

Electric energy is to be also supplied to a heater assembly 40. The heater assembly 40 is mounted within a media tank 42. The maximum volumetric size for the media tank 42 will generally be forty liters. However, it is considered to be within the scope of this invention that this can be readily changed. Media 44 is to be supplied through the open top 46 of the media tank 42. The open top 46 is then covered by a tank cover 48 with the tank cover 48 having ventilation holes 50. It is to be understood that the media 44 will comprise a liquid which is basically similar to water and actually will comprise a mild hydrochloric solution. This solution will essentially duplicate the liquid which is normally contained within the stomach of a human being.

After activation of the media dispensing apparatus 10 by means of the control panel 22, heater assembly 40 is activated and sufficient time is permitted to heat the media 44 to the desired temperature level within the media tank 42. The media 44 is then to be pumped to the vessels 52. There are to be seven in number of the vessels 52 with these vessels 52 being mounted within a frame 54 which is mounted on the upstanding section 20. Each of the vessels 52 are identical in volume. There is to be an individual fill line 56 for each vessel 52 with it being understood that there are seven in number of separate fill lines 56. Fill lines 56 extend from the fill manifold 58. The media 44 is conducted through an outlet line 60 from the media tank 42. The outlet line 60 connects to a five micron filter 62 which is mounted within the media tank 42.

Fill manifold 58 connects to each vessel 52 by the fill lines 56 with each fill line 56 connecting to a discharge tube 64 which is mounted within the vessel 52. Each of the fill lines 56 is conducted through a pinch valve assembly 66. The discharge tube 64 for each vessel 52 has mounted thereon a fixed mounting bracket 68 and a pointer handle 70. Fixedly attached to the fixed mounting bracket 68 is a vertical bar 72. The vertical bar 72 is mounted on its lower end to crossbar 74. The crossbar 74 is to be fixedly mounted onto its respective vessel 52 with it being understood that there is a separate crossbar 74 for each vessel 52. The vertical bar 72 includes a series of notches 76. The pointer handle 70 is fixed onto its respective discharge tube 64. The pointer handle 70 can be pivoted to disengage from a notch 76 and then the discharge tube 64 moved relative to the vessel 52 which also moves the discharge tube 64 relative to the fixed mounting bracket 68. Each notch 76 is to denote a precise volume within the vessel 52. The volumetric difference between directly adjacent notches 76 amounts to fifty milliliters. The precise volume is to occur when the surface level of the media 44 aligns with the dispensing opening 78 of the discharge tube 64.

Also mounted in conjunction with each vessel 52 is a dispense tube 80. The dispense tube 80 extends all the way to the bottom of its vessel 52. It is to be understood that there is a separate dispense tube 80 for each vessel 52. Media 44 is to be able to flow from the dispense tube 80, into the dispense line 82 with it being understood that there is a separate dispense line 82 for each vessel 52. Each dispense line 82 passes through the pinch valve assembly 66 and connects to a dispense manifold 84. The dispense manifold 84 has eight in number of outlet tubes 86. These outlet tubes 86 are precisely positioned on the dispense manifold 84. Each of the fill lines 56 that connect to the dispense manifold 84 are connected by a quick disconnect mechanism, which is not shown. The dispense manifold 84 is to be placed in conjunction with the vessels of a dissolution test apparatus, which is not shown. Each outlet tube 86 is to connect with a separate vessel of the dissolution test apparatus and all the outlet tubes 86 are located on the dispense manifold 84 so that there will be a separate outlet tube 86 connecting to a separate vessel of the dissolution test apparatus. For example, in some dissolution test apparatuses there are eight in number of such vessels and the outlet tubes 86 are represented in FIGS. 4–7 by circled areas 88 in conjunction with the dispense manifold 84. The circled areas 88 are numbered 1–8 which correspond to the eight different vessels of the dissolution test apparatus. If there are a lesser number of vessels in the dissolution test apparatus, the fill line 56 for the not-available vessels is to be disconnected by the quick disconnect mechanism, thereby not using of that fill line 56.

The vertical bars 72 will include indicia dividing the incremental bar into a series of increments. Typical divisions would be between two hundred and fifty milliliters and one thousand milliliters with the number one thousand being located directly adjacent the fixed mounting bracket 68. By adjusting of the pointer handle 70 and having it engage with the notch 76 that corresponds to a particular desired volume indicia which is inscribed on the vertical bar 72, this will determine the amount of media 44 that will be contained within the vessel 52. How this occurs will be explained further on in the specification.

The pumps 30 and 32 each have a pressure side and a vacuum side. The vacuum side of the pump 32 connects to the pressure vacuum manifold 90. The pressure vacuum manifold 90 has a conduit 92 which connects through an orifice 94 to the vessel 52. It is to be understood that there is a separate conduit 92 for each vessel 52 and all the conduits 92 connect directly to the manifold 90. Connecting with each of the conduits 92 is a conduit 96. There is only a single conduit 96 with this conduit connecting with discharge tube 98 which is mounted within an overflow vessel 100. The function of the overflow vessel 100 will be explained further on in the description. The overflow vessel 100 will be mounted in the arrangement of the vessels 52 that are mounted within the frame 54. A separate conduit 102 connects with the overflow vessel 100 with the separate conduit 102 branching off into separate branches with one branch connecting with valve 104 and the second branch connecting with valve 106. Valve 104 connects with pressurized air supply conduit 108 with valve 106 connecting with vacuum conduit 110. Vacuum conduit 110 connects with pump 32.

The outlets of the pumps 30 and 32 connects to a connecting conduit 112. Mounted within the connecting conduit 112 is an orifice 114. The pump 30 is preset to operate at about 35 psi. The pump 32 is set to operate at about 10 psi. The pressure is to be adjusted for pump 30 by pressure adjust 116. A factory preset pressure adjust 118 is to be used to set the pressure for pump 32 at 10 psi.

The output of pump 30 connects with the conduit 120. Conduit 120 connects with valves 122 and 124. Valve 122 is connected to a conduit 126 which in turn connects with the pinch valve assembly 66. The valve 124 connects with the conduit 128 which also connects with the pinch valve assembly 66.

The operation of the media dispensing apparatus 10 of this invention as follows: Once the media apparatus 10 has been turned to the "on" position by the switch 38 with the plug 36 connecting with the source of electrical energy and media has been filled within the tank 42 and the media 44 is being heated by the heater assembly 40 to the desired temperature, the user activates the control panel 22 which will now automatically cause the following series of events to occur. Prior to initiating of the control panel 22, the pointer handle 70 of each vertical bar 72 has been adjusted to a particular desired volume level. This will locate the dispensing opening 78 at a particular vertical height within its respective vessel 52. Generally, all vessels 52 will be set so that each will receive the same volume. With the pumps 30 and 32 being activated, vacuum is drawn within the pressure vacuum manifold 90 and through the orifice 94 into each of the vessels 52. The orifice 94 is of a size of approximately 0.032 inches. The purpose of the orifice 94 is to limit the flow amount of pressure or vacuum within each of the vessels 52 and not cause a pressure or vacuum surge within any one of the vessels 52. Vacuum is also drawn through conduit 110, valve 106, conduit 102 into overflow vessel 100. The pressure from the pump 30 is conducted through conduit 120 and 128 to pinch valve assembly 66. This will cause the pinch valve assembly 66 to move pinch bar 130 to the position shown in FIG. 4 of the drawings. The result is the dispensing lines 82 are closed so there is no media being conducted into each of the dispensing tubes 80. It is to be understood that there may be as many as eight in number of the dispensing lines 82 with each dispensing line 82 connecting with an outlet tube 86 with the outlet tubes 86 being represented by circled areas 88. Although there are eight in number of the circled areas 88, there will actually only be used seven of the circled areas 88 since there will only be seven vessels 52. However, at some later time, a media dispensing apparatus 10 may be developed that has eight in number of the vessels 52 and it is for this reason that the eighth circled area 88 is provided.

Figure 4:
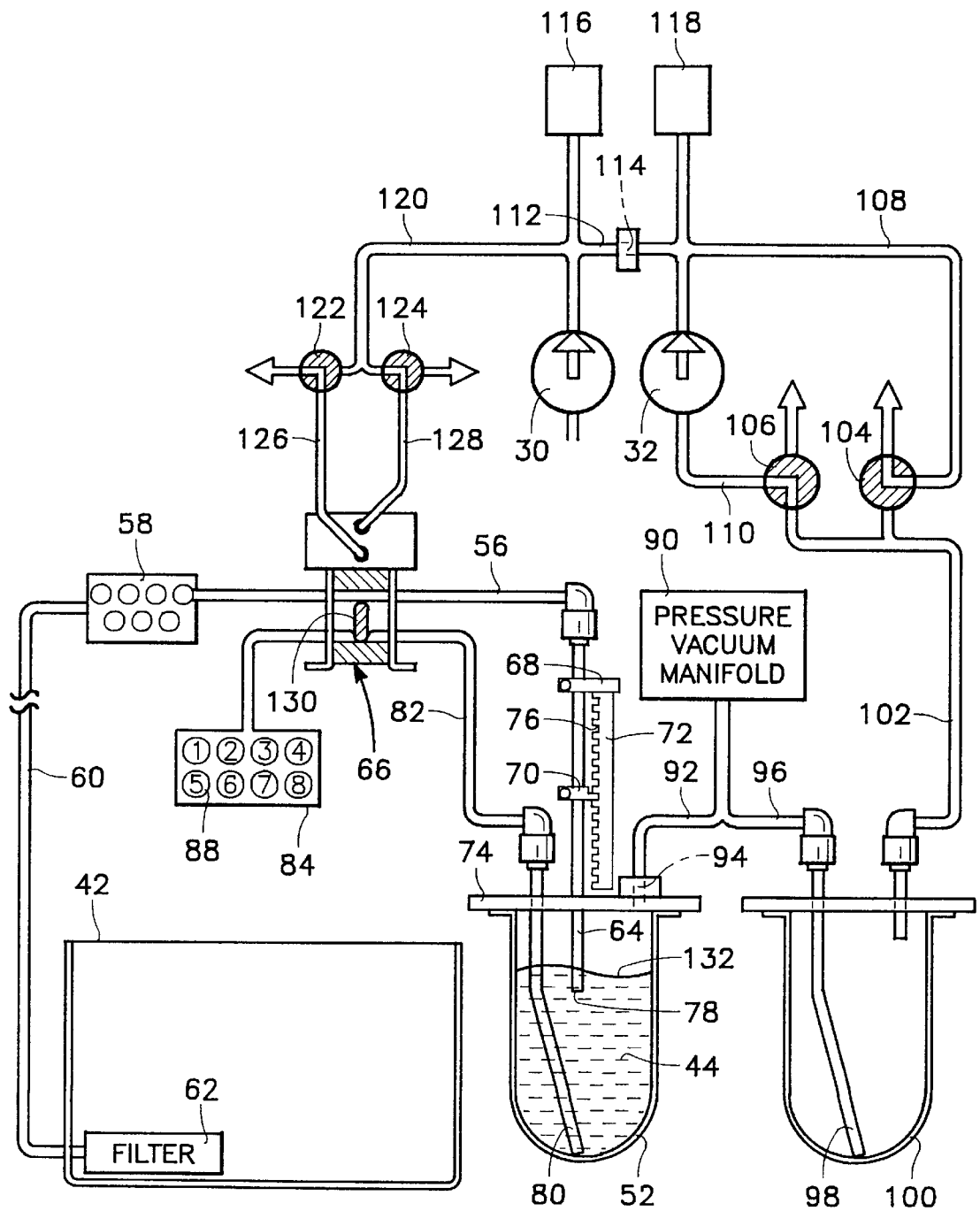
FIG. 4 is a flow diagram of the media dispensing apparatus of the present invention depicting the position of the apparatus during the fill cycle, that is filling of the vessels within the media dispensing apparatus.
Figure 5:
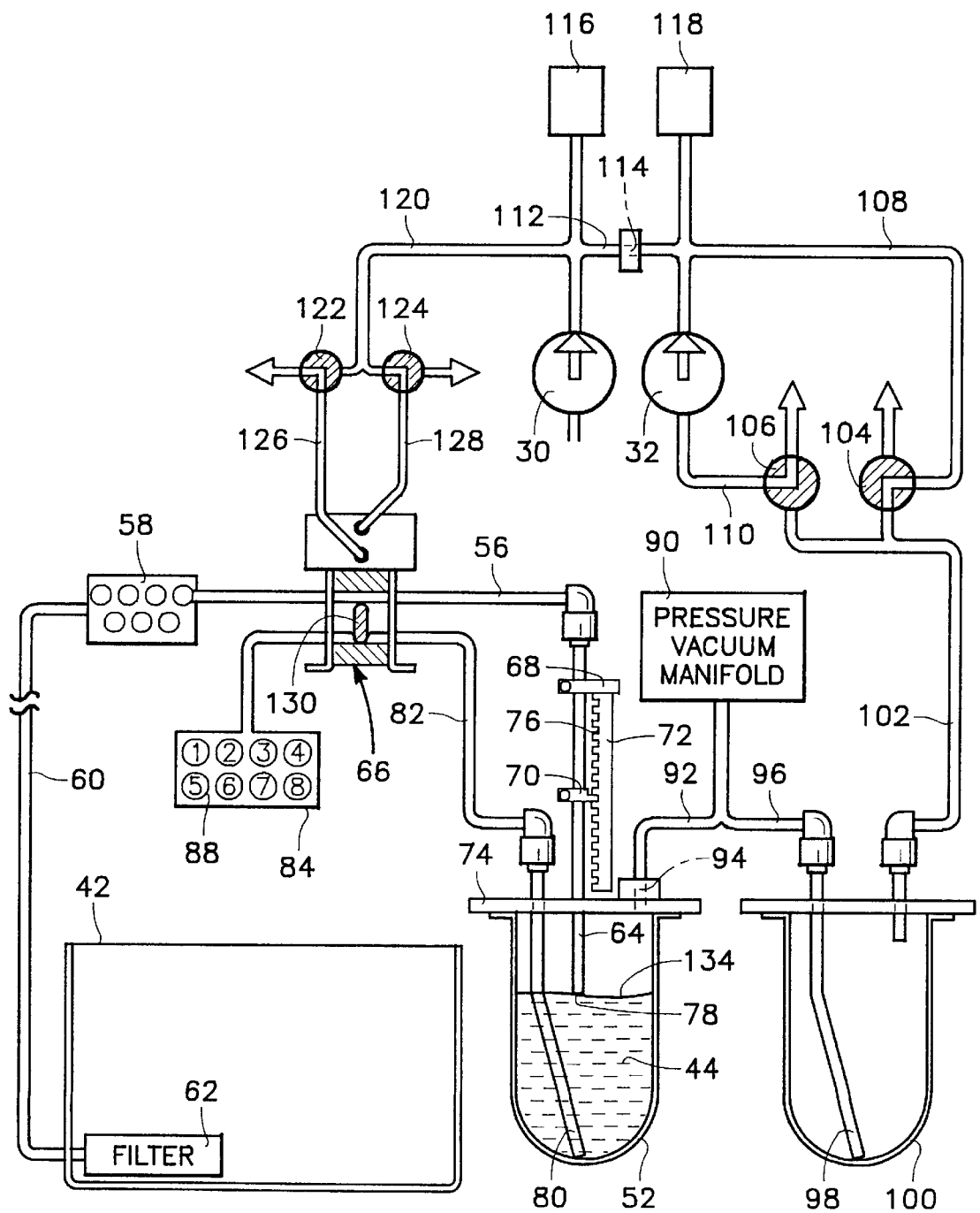
FIG. 5 is a flow diagram, similar to FIG. 3, but showing the flow diagram in the position with the media contained within the vessels of the media dispensing apparatus located at the precise volume level that is to be then dispensed to the dissolution test apparatus.

In referring to FIG. 4, the vacuum side of the pump 32 is being supplied through valve 106 and conduit 102 into the overflow vessel 100. Normally, there will not be any media contained within the overflow vessel 100 with the result that the vacuum is conducted directly through discharge tube 98, conduit 96 and into conduit 92 and also the pressure manifold 90. Within the pressure vacuum manifold 90, vacuum is conducted into the other conduits 92 since there is a conduit 92 for each vessel 52. Vacuum within the conduit 92 is restricted through the orifice 94. The restriction of the orifice 94 prevents a vacuum surge within any particular vessel 52. The media 44 is then caused by the vacuum contained within each of the vessels 52 to be drawn into each vessel 52 since the vacuum would be conducted through the discharge 64, fill line 56, outlet line 60 through the filter 62 into the media tank 42. Therefore, media 44 will be caused to flow into each of the vessels 52. This is to continue until the media 44 reaches a level 132 which is at some distance between the dispensing opening 78 and the crossbar 74. Because a vacuum is still being supplied within the air space above the level 132 within each vessel 52 (each vessel 52 is closed to the ambient), media still continues to flow through the discharge tubes 64 even though the dispensing opening is submerged within the media 44 in the vessel 52. This drawing of the vacuum in the air space above the media 44 in each pressure vessel 52 causes the media 44 in that pressure vessel 52 to be deaerated. That air is being pumped by the pump 32 out through conduit 108 through valve 104 into the ambient. If, per chance, one or more of the vessels 52 overfills with media 44 being caused to flow through the orifices 94 and conduit 90 prior to reaching the pressure vacuum manifold, 90 the overflow media 44 is caused to flow through conduit 96 into the discharge tube 98 of the overflow vessel 100. Even with media 44 in the overflow vessel 100, as long as the vacuum is being drawn through the conduit 102 into the overflow vessel 100, there still will be a flowing of media 44 into each of the vessels 52. However, control panel 22 will normally stop the fill cycle prior to any overflowing into the overflow vessel 100.

Now it is desired to locate the precise volume of the media within each of the vessels 52 which has been preset by each pointer handle 70. This is accomplished as represented within FIG. 5. The pinch bar 130 remains in the same position as in FIG. 4. However, conduit 102 through valve 104 is cause to connect to the pressure side of the pump 32 which is connected to conduit 108. This pressure side is about 10 psi. This 10 psi pressure is supplied through the conduit 102 into the overflow vessel 100. Normally, there will not be any liquid contained within the overflow vessel 100 and this pressure will be supplied through the discharge tube 98 to the manifold 90 and then be distributed through each conduit 92 through each orifice 94 into each vessel 52. This pressure is supplied into the air space of each vessel 52 with this pressure causing the media 44 to be discharged into the discharge tube 64 through their respective fill line 56, outlet line 60, through the filter 62 and back into the media tank 42. The surface level 132 of the media 44 is lowered to the dispensing opening 78 which is now represented by the surface level 134 in FIG. 5. Further air pressure will now only result in air being discharged through the discharge tube 64, fill line 56, outlet line 60 and through the filter 62 into the media tank 42. The result is the volumetric level within each vessel 52 is precisely aligned with the dispensing opening 78. The position of the dispensing opening 78 is preset by the volumetric determination established by the position of pointer handle 70 for each vessel 52. This volumetric determination is exceedingly precise as in dissolution test equipment it is necessary that the volumetric determinations for each vessel be identical and precisely determined.

The procedure at this time is to now dispense the media 44 contained within each of the vessels 52 with the amount of media 44 in each vessel 52 being discharged into an individual testing vessel or flask of a dissolution test apparatus which has not been shown. In other words, the media 44 of each vessel 52 is merely transferred to a similar type of vessel (not shown) within the dissolution test apparatus. In order to accomplish this, reference is to be had to FIG. 6 for the position of the valves 122 and 124 is reversed which causes the pinch valve assembly 66 to be operated moving of the pinch bar 130 to close the flow lines 56. The dispensing lines 82 are now open. The operator will have physically placed the dispense manifold 84 in conjunction with the vessels of the dissolution test apparatus so that each outlet tube 86 will connect with a separate vessel of the dissolution test apparatus. Air pressure is still being supplied into each vessel 52 with the result that the media is being forced through each of the dispensing tubes 80, through the dispensing lines 82 to the dispensing manifold 84. The pressure within each of the vessels 52 continue until the amount of media 44 that is contained in each vessel 52 has been completely emptied therefrom and is now located within the respective vessels of the dissolution test apparatus. The result is that precisely the same volume of media 44 has been supplied to each of the vessels of the dissolution test apparatus. This media 44 is also located at the precise desired temperature. This media 44 has also been de-aerated.

Figure 6:
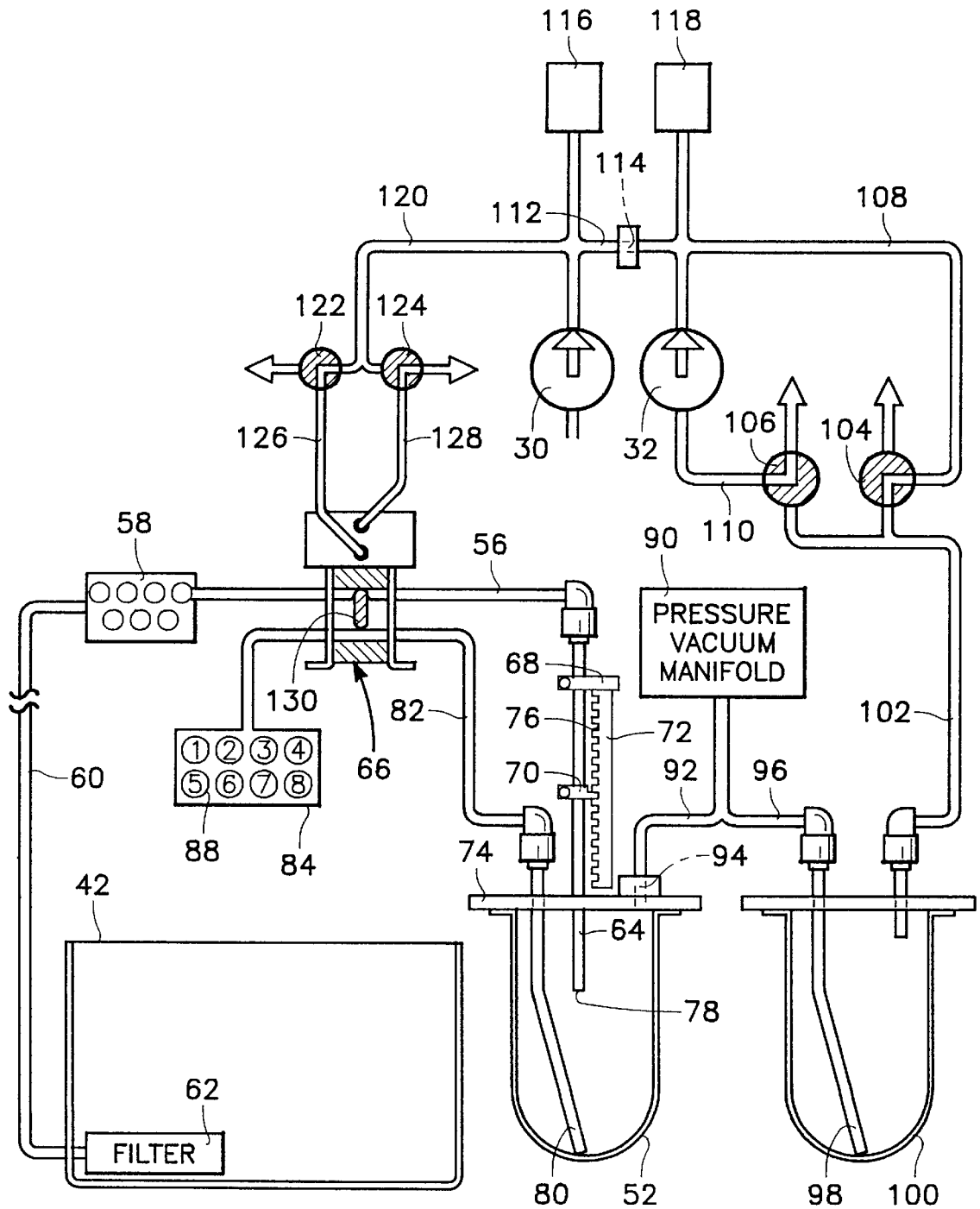
FIG. 6 is a flow diagram, similar to FIG. 4, showing the flow diagram in the position after dispensing of the media from the vessels of the media dispensing apparatus.
Figure 7:
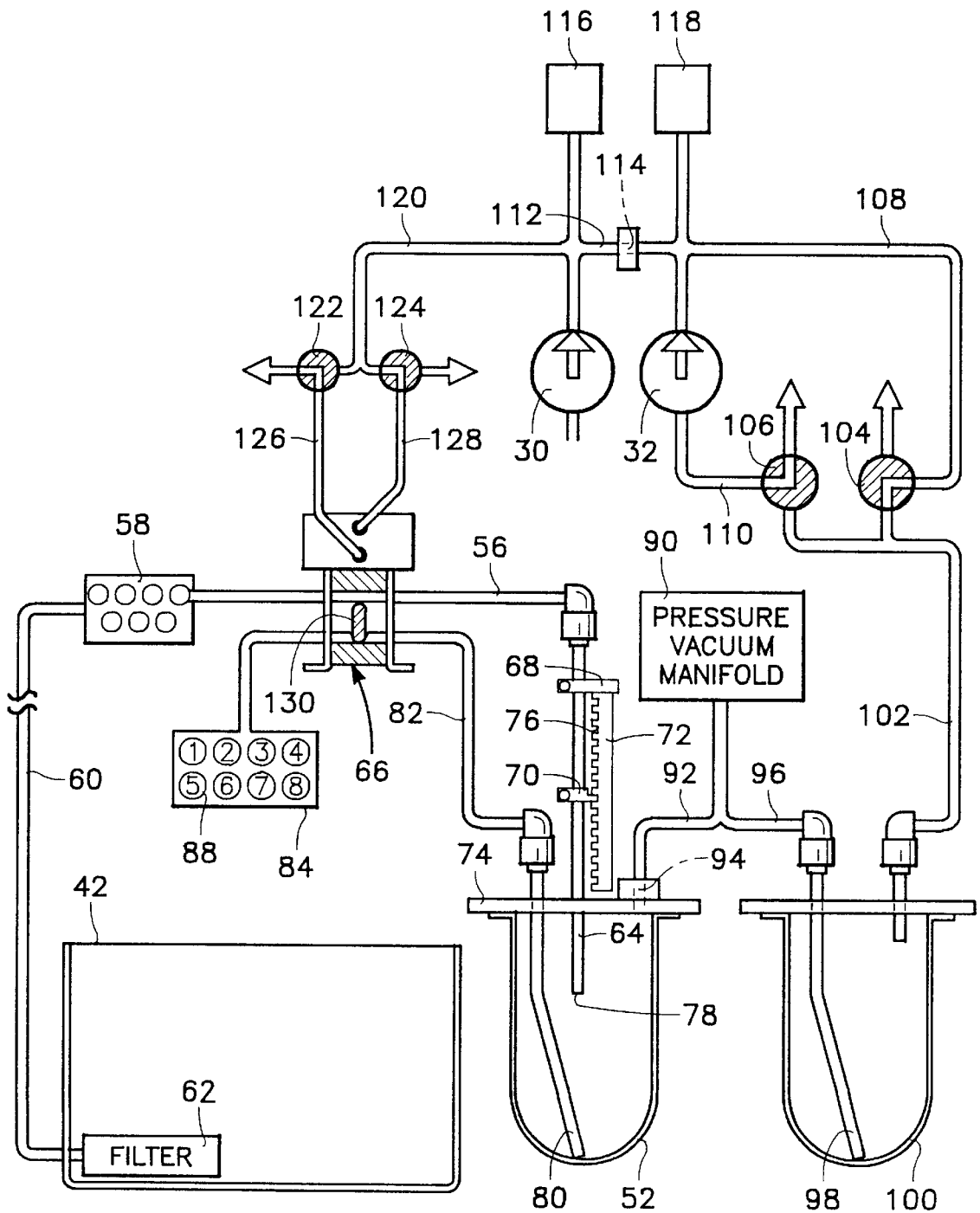
FIG. 7 is a flow diagram, similar to FIG. 6, showing the apparatus of the present invention in the stand-by position waiting for a command from the operator to start a cycle.

After the dispensing mode shown in FIG. 6, the media dispensing apparatus 10 will then be placed by the control panel 22 into a stand-by mode which is shown in FIG. 7. In the stand-by mode, the pinch bar 130 is moved to close off the dispensing lines 82 and open fill lines 56. However, there is no media 44 located in any of the vessels 52 so only air is now being conducted through the fill lines 56, into the fill manifold 58 and through the outlet line 60, through the filter 62 into the media tank 42. The purpose of this air being discharged into the media tank 42 will function to create a turbulent action within the media 44 contained within the media tank 42 which will help to have the overall temperature of the media 44 to be constant throughout the entire volume of the media tank 42. From the stand-by mode of FIG. 7, the sequential operating procedure can be repeated for a new series of vessels 52 with probably an additional supply of media 44 being supplied into the media tank 42 prior to the initiating of the sequential operations represented by FIGS. 4–6.

It is important that the pinch valve 66 always be able to operate. For this reason, the orifice 114, of 0.026 inches, is located within the connecting conduit 112. Since the output of the pump 30 is about three and one-half times greater pressure than the output of pump 32, and since the orifice 114 restricts the flow of air into conduit 108, there will always be supplied sufficient pressure to operate the pinch valve assembly 66 even if, for some reason, all the outlets of pump 32 freely discharge into the atmosphere. The pressurized output of pump 30 is to be added to the output of pump 32 in conduit 108. The sizes of the outlets of each of the pumps 30 and 32 will normally be about one-quarter of an inch in diameter. The orifices 94 are sufficiently restricted that if the operator, for whatever reason, only desires to fill one of the vessels 52, that sufficient vacuum would be applied to that vessel 52 to cause that vessel 52 to overfill and by reversing the pressure cause that vessel to be located at the precise volume that was preselected.

What is claimed:

1. A media dispensing apparatus comprising:
  a portable cart having a plurality of vessels, each said vessel having a discharge tube, a fill line connecting to each said discharge tube with there being a separate said fill line for each said discharge tube;
  a media tank included with said portable cart, said media tank adapted to contain a supply volume of media, a fill manifold mounted on said portable cart, said media tank to supply media to said fill manifold, each said fill line being connected to said fill manifold, said fill manifold to supply media from said media tank into each said vessel; and a dispense tube mounted in each said vessel with there being a separate said dispense tube for each said vessel, a dispense line connecting with each said dispense tube with there being a separate said dispense line for each said dispense tube, a dispense manifold mounted on said portable cart, each said dispense line being connected to said dispense manifold, a plurality of outlet tubes connected to said dispense manifold, media from a said vessel is to flow through said dispense tube and then into said dispense manifold and then into a respective said outlet tube to then be dispensed exteriorly of said portable cart.

2. The media dispensing apparatus as defined in claim 1 wherein:

a valve assembly mounted in conjunction with each said fill line, each said fill line to be simultaneously opened and closed by said valve assembly.

3. The media dispensing apparatus as defined in claim 1 wherein:

a valve assembly mounted in conjunction with each said dispense line, each said dispense line to be simultaneously opened and closed by said valve assembly.

4. The media dispensing apparatus as defined in claim 1 wherein:

a valve assembly mounted in conjunction with each said fill line and each said dispense line, said valve assembly to be movable between a position closing of said fill lines and leaving said dispense lines open and a position closing of said dispense lines and leaving said fill lines open.

5. The media dispensing apparatus as defined in claim 1 where in:

deaerating means mounted on, said portable cart for deaerating the media contained within each said vessel.

6. The media dispensing apparatus as defined in claim 1 wherein:

an overflow vessel mounted within said portable cart, said overflow vessel to receive any over supply of media to any of said vessels.

7. The media dispensing apparatus as defined in claim 1 wherein:

a filter mounted within said media tank, the media to pass through said filter prior to flowing into each said fill line.

* * * * *